United States Patent [19]
Dickason

[11] 3,987,078

[45] Oct. 19, 1976

[54] AMMOXIDATION PROCESS FOR MAKING 2,6-DICYANONAPHTHALENE

[75] Inventor: Alan F. Dickason, Chester, Pa.

[73] Assignee: Suntech, Inc., St. Davids, Pa.

[22] Filed: Oct. 29, 1975

[21] Appl. No.: 626,803

[52] U.S. Cl. .......................... 260/465 C; 252/432; 252/474; 252/476
[51] Int. Cl.$^2$ ...................... C07C 120/14
[58] Field of Search .................. 260/465 C

[56] References Cited
UNITED STATES PATENTS

| | | | |
|---|---|---|---|
| 3,637,797 | 1/1972 | Decker et al. | 260/465 C |
| 3,812,171 | 5/1974 | Neikam et al. | 260/465 C |

FOREIGN PATENTS OR APPLICATIONS

| | | |
|---|---|---|
| 41-16511 | 9/1966 | Japan |
| 42-9818 | 5/1967 | Japan |

*Primary Examiner*—Lewis Gotts
*Assistant Examiner*—Dolph H. Torrence
*Attorney, Agent, or Firm*—J. Edward Hess; Donald R. Johnson; Paul Lipsitz

[57] ABSTRACT

In the process of making 2,6-dicyanonaphthalene by reacting 2,6-dimethylnaphthalene, ammonia and oxygen under ammoxidation conditions at atmospheric pressure, the improvement which comprises carrying out said ammoxidation in the presence of an unsupported alkali-metal vanadium bronze catalyst, optionally promoted with titanium, boron or iron and with a molar ratio of ammonia to 2,6-dimethylnaphthalene of at least about 25:1.

7 Claims, No Drawings

AMMOXIDATION PROCESS FOR MAKING 2,6-DICYANONAPHTHALENE

It is known in the art to effect ammoxidation of aromatic hydrocarbons such as alkylated benzenes and naphthalenes with ammonia and oxygen to obtain the corresponding nitriles. Wide reaction conditions and numerous types of catalysts have been employed for such reactions including vanadium oxides either alone or promoted with one or more different metals. In British Patent 977,755 it is disclosed that alkylated compounds generally, but particularly those of the benzene series (e.g., toluene, the xylenes, etc.) and alkyl-substituted pyridines may be converted to the corresponding nitriles by ammoxidation using 3 to 10 times the stoichiometric ratio of ammonia to hydrocarbon and employing as catalyst an oxygen containing compound with or without promoters such as oxides of titanium, iron, vanadium and others.

In British Patent 1,319,287 an ammoxidation process for alkylated benzene hydrocarbons is disclosed using as catalyst a mixture of vanadium oxide and molybdenum oxide and the mole ratio of ammonia to hydrocarbon is given desirably as 4 to 14 with the comment that "little sense lies in employing more than 12 moles of ammonia per mole of hydrocarbon, since an increase in yield cannot be obtained thereby".

In U.S. Pat. No. 3,433,823 ammoxidation of methyl aromatic compounds such as toluene, xylene, methylnaphthalene, 1,4-dimethylnaphthalene, and the like is disclosed using as catalyst a mixture of a vanadium polyphosphate and one oxide of molybdenum, copper, tungsten, thorium, uranium or zirconium and where the ammonia to hydrocarbon mole ratio is given as 0.2 to 20, preferably 1 to 10.

The numerous disclosures in the prior art of ammoxidation such as those given above generally consider the alkylated benzenes and alkylated naphthalenes to be equivalent in their reaction with ammonia and oxygen. However, experimental work has shown that in the case of 2,6-dimethylnaphthalene the reaction parameters of the prior art do not enable ammoxidation to be achieved in a manner suitable for an economically viable process. For example, with prior art conditions, the 2,6-dicyanonaphthalene is obtained with low selectivity or if selectivity is high initially, it quickly falls as the reaction continues to unacceptably low levels.

In accord with the process of this invention 2,6-dicyanonaphthalene is obtained with high selectivity which is maintained for extended times by reacting 2,6-dimethylnaphthalene, ammonia, and oxygen under ammoxidation conditions and in the presence of an unsupported alkali-metal-vanadium bronze catalyst optionally promoted with titanium, boron, or iron and employing a mole ratio of ammonia to 2,6-dimethylnaphthalene of at least about 25:1.

The process of the invention is carried out in either a fixed or fluidized bed mode of operation at a temperature between about 375° C. and 550° C., preferably 400° C. to 450° C., most preferably about 425° C. to 435° C. at essentially atmospheric pressure. The source of oxygen is preferably air, but any oxygen source is suitable. The amount of oxygen used in the process may vary over wide limits, but the process enables rather limited amounts of oxygen to be used and this, in turn, is favorable in that less burn of hydrocarbon reactant occurs. Thus, the ratio of oxygen to xylene hydrocarbon in the reactant stream will usually be up to about 6:1, although it is preferable to use no more than about 5:1, preferably 2.5:1 to 4.5:1. The ratio of ammonia to hydrocarbon used in the process of the invention is critical for obtaining high nitrile selectivity for continuing periods and will be at least about 25:1. Ratios of ammonia to hydrocarbon of up to 100:1 have been shown to be useful, but, in general, ratios of from about 25:1 to about 50:1 will be preferred.

It will be understood that the contact time for the reactants over the catalyst will vary over a wide range, but will usually be from about 0.1 to 30 seconds. The contact time actually used will depend upon catalyst loading, catalyst volume, temperature and other parameters and the skilled art worker will have no difficulty in selecting an appropriate contact time dependent upon these reaction parameters.

The reactant feed stream, will, of course, contain other materials, as for example, the inert ingredients of air, recycled 2,6-dimethylnaphthalene, and possibly some small amounts of other by-products associated with the recycle stream. This use of a recycle stream will make possible a still more efficient process.

In addition to the above required parameters of the process it is essential that a particular type of material be used as catalyst. It is known in the art that the addition of an alkali metal compound to vanadium pentoxide will, when the mixture is heated yield complex materials with anomalous valencies known as a vanadium bronzes. Such lithium bronzes are discussed by Volkov et al., Zh. Neorg. Khim: 17 (6): 1529–1532 (1972). Vanadium bronzes with sodium are described by Pouchard et al, Bull de la Soc. Chimique de France, No 7, pages 274245 (1968), and No. 11 pages 43434348 (1967). Similarly, potassium containing vanadium bronzes are discussed by Holtzberg et al., J. Am. Chem, Soc. Vol. 78, pages 1536–40 (1956). Lithium bronzes are described by Hardy et al., Bull de la Soc. Chimique de France, No. 4, 1056–65 (1965) and by Reisman et al Jour. Physical Chemistry 66 1181–85 (1962). Also of interest is the article by P. Hagenmuller entitled "Tungsten Bronzes, Comprehensive Inorganic Chemistry", edited by J. S. Bailar, Jr. et al. and published in 1973 by Pergamon Press.

All of the above references as well as the references which follow are hereby incorporated herein to teach the chemistry and preparation of the bronzes which are used in this invention.

These bronze materials are prepared by mixing an appropriate alkali metal compound (e.g., carbonate, oxalate, etc.) with vanadium pentoxide and heating the mixture at an elevated temperature for several hours. Depending upon the amount of alkali metal ion added certain phases will be established in accordance with the particular phase diagram pertinent to the mixture. Thus, for example, the Holtzberg et al. article referred to above describes the potassium bronze system and the sodium system is shown in the article by Slobodin et al., J. Appl. Chem., (USSR) Vol. 38, pp 799803 (April 1965). Of the above alkali metal vanadium bronzes, all of which may be used in the process of the invention, the preferred bronzes for use as catalysts are the sodium bronzes and mixtures of the various species also may be employed. Preferred species include Bronze I (BZ I) which has an atomic ratio of sodium to vanadium of 0.167, Bronze II (BZ II) where the atomic ratio is 0.417, and an alpha prime phase ($\alpha'$ - phase) where the atomic ratio is 0.50. The terms Bronze I and Bronze II are used herein because these compounds correspond to the compounds called "first BRONZE" and "second BRONZE" by Slobovin and Fotiev, Jour. Applied Chemistry (USSR) 38 Vol. 4 pg. 799 April 1965 where the first bronze is characterized by having 14.3 mole percent of $Na_2O$ in its composition (as does BZ I) and the second bronze has 29.4 mole percent of $Na_2O$ (as does BZ II). These preferred Bronze I and $\alpha'$-phase bronzes may be further characterized by the generic empirical formula $Na_xV_2O_5$ where x is greater than zero and equal to or less than 1. Other bronze systems of the $Na_xV_2O_5$ species are known where x is greater than 1 and these are useful in the process, but are somewhat unstable and therefore not preferred. The BZ I species may be considered as $Na_2O \cdot V_2O_4 \cdot 5V_2O_5$ or $Na_{0.33}V_2O_5$ which is shown together with related members of the series at pages 573 to 575 of the Hagenmuller article as $\beta$-$Na_xV_2O_5$ where $x$ varies from 0.22 to 0.40, the $\beta$ designation indicating the particular crystal phase structure of the compound. The BZ II species may be considered as $5Na_2O \cdot V_2O_4 \cdot 11V_2O_5$ or as $Na_{1+x}V_3O_8$ (x = 0.25) which is isotypic with $Li_{1+x}V_3O_8$ and is shown at page 584 of the Hagenmuller article mentioned above. The $\alpha'$-phase is characterized as $Na_xV_2O_5$ where $x = 0.7$ to 1.0 (see page 577 of the Hagenmuller article). Also characteristic of the bronzes are their x-ray diffraction patterns wherein the strongest lines are as follows:

BZ I: 9.6, 7.3, 4.75, 3.87, 3.47, 3.38, 3.21, 3.11, 3.08, 2.92, 2.90, 2.727, 2.55, 2.45, 2.38, 2.18, 1.97, 1.87, 2.803, 1.74, 1.535, 1.492.

BZ II: 6.9, 7.04, 5.81, 3.87, 3.62, 3.50, 3.45, 3.21, 3.10, 3.01, 3.67, 2.57, 2.43, 2.32, 2.27, 2.02, 1.97, 1.96, 1.81, 1.72, 1.86, 1.504, 1.333, 1.39.

$\alpha'$-phase: 11.3, 5.645, 4.82, 4.436, 3.667, 3.456, 2.967, 2.889, 2.882, 2.799, 2.604, 2.436, 2.412, 2.291, 2.0196, 1.889, 1.803, 1.77, 1.689, 1.635, 1.592, 1.479.

The $\alpha$-prime phase as with the other bronzes may be obtained by the methods described in the literature and placed on the support for use in the process, or it may be made in situ. This is readily achieved by treating the BZ II on the support with a reducing atmosphere (e.g., ammonia) or a stream similar to the hydrocarbon, ammonia and oxygen; e.g., an oxygen to hydrocarbon mole ratio of less than about 3.0.

As indicated the catalyst bronzes may comprise a mixture of the above discussed bronzes and preferred catalysts will comprise a mixture predominant in either BZ II or the $\alpha$-prime phase or both. While BZ I used above is operable, it is preferred in order to keep the carbon oxides to a minimum to avoid having a predominant amount of BZ I in the catalyst composition.

In order to obtain the metal promoted catalyst used in the invention, the appropriate metal compound is simply added during the catalyst preparation. Preferably, the metal oxide will be employed as the promoter and, as indicated, the catalyst will contain titanium and boron and may, optionally, contain iron. One technique for preparing the catalyst is to physically mix the powdered catalyst ingredients and press the mixture into pellets for use.

In one technique the promoter oxide is added to all of the powdered catalyst ingredients and physically mixed and the mixture pressed into pellets for use. In another technique, a water soluble metal compound (e.g., boric acid, ferric potassium oxalate, titanium oxalate, etc.) is added to the other catalyst ingredients. The promoted catalyst composition will contain the vanadium bronze in an amount of from about 30% to 90% by weight expressed as $V_2O_5$, the balance being one or more of the promoting metals.

The catalyst composition of the invention is thus an alkali metal vanadium bronze or an alkali metal vanadium bronze promoted with one or more of titanium, boron, or preferably iron and the alkali metal vanadium bronze is preferably Bronze II or the $\alpha$-prime phase. The catalysts are preferably pelletized for use, but may also be employed in powder form.

EXAMPLE 1

Preparation of Catalyst

An unsupported sodium-vanadium bronze promoted with titanium, boron and iron was prepared as follows:

An unsupported sodium-vanadium bronze catalyst promoted with titanium, boron and iron was prepared by mixing the dry ingredients together in a rolling jar mixer for fifteen (15) minutes. The dry mixture was added to 150 - 200 mls of water at room temperature then stirred for 30 minutes. The resulting suspension was dried on a steam bath for fifteen (15) minutes after which the catalyst paste was spread on a pellet plate. The pellet plate was dried in a vacuum oven at 144° C for three hours and then calcined in a muffle furnace for four hours at 540° C.

The dry mixture was prepared by adding the following ingredients together in parts by weight:

$V_2O_5$ — 61.8
$TiO_2$ — 27.3
$Na_2O$ — 8.4
$H_3BO_3$ — 2.0
$Fe_2O_3$ — 0.5

The final catalyst composition which is a promoted sodium-vanadium bronze conformed to a mixture expressed as oxides, of 1 mole $V_2O_5$, 0.4 moles $Na_2O$, 1 mole $TiO_2$, 0.05 moles $B_2O_3$, and 0.01 mole $Fe_2O_3$. The amount of vanadium, expressed as oxide, was 41% by weight.

EXAMPLE 2

The ammoxidation reaction was carried out with a fixed bed containing the catalyst of Example 1 using stainless steel tubular reactors varying in size of outside diameter of from 0.25 in. to 1.0 in. and heated by means of a sand bath or a split core tube furnace.

The reaction conditions and results obtained are shown in the following table.

TABLE I

Ammoxidation of 2,6-Dimethylnaphthalene (2,6-DMN)

catalyst: Sodium Vanadium Bronze Promoted With Titanium, Boron and Iron  
Pressure: 1 Atmosphere  
Contact Time 1.8 sec.  
Conc. of Hydrocarbon In Feed Stream: 2.9 %

| RUN NO. | Temp. °C | Mole Ratio $O_2$:2,6-DMN | Mole Ratio $NH_3$:2,6-DMN | % Conversion | % Selectivity | TIME (hrs) |
|---|---|---|---|---|---|---|
|  | 450 | 1.5 | 2.9 | 10 | 72 | 12.5 |
| 2 | 449 | 3.0 | 3.4 | 21 | 66 | 1.9 |
|  | 449 | 3.1 | 3.4 | 15 | 56 | 2.9 |
| 3 | 450 | 1.6 | 8.8 | 14 | 78 | 6.5 |
|  | 450 | 1.6 | 8.4 | 16 | 82 | 7.5 |
|  | 450 | 1.4 | 8.7 | 9 | 70 | 10.2 |
| 4 | 450 | 1.9 | 10.0 | 19 | 85 | 3.9 |
|  | 450 | 1.9 | 10.0 | 21 | 74 | 4.3 |
| 5 | 397 | 3.2 | 17.5 | 45 | 96 | 1.0 |
|  | 397 | 4.2 | 17.5 | 51 | 91 | 2.0 |
|  | 393 | 4.2 | 17.9 | 36 | 86 | 7.3 |
| 6 | 403 | 4.2 | 18.7 | 35 | 92 | 1.2 |
|  | 403 | 4.2 | 19.1 | 39 | 92 | 2.6 |
|  | 403 | 4.2 | 18.8 | 38 | 91 | 6.2 |
|  | 403 | 4.1 | 18.7 | 35 | 87 | 7.0 |
|  | 393 | 4.3 | 18.3 | 40 | 83 | 11.0 |
| 7 | 403 | 4.4 | 33.0 | 33 | 92 | 4.4 |
|  | 398 | 4.3 | 33.0 | 36 | 92 | 8.6 |

As can be seen from the above data in runs 2 through 6, the selectivity to 2,6-dycyanonaphthalene quickly drops off after only a few hours on stream. On the other hand, run 7 shows that with the high mole ratio of ammonia to 2,6-DMN, a high selectivity is maintained for more than 8 hours without evidence of a decrease.

EXAMPLE 3

An unsupported vanadium catalyst promoted with titanium and boron was prepared by mixing the dry ingredients together in a rolling jar mixer for 15 minutes. The dry mixture was added to 150 – 200 mls of water at room temperature then stirred for 30 minutes. The resulting suspension was dried on a steam bath for fifteen (15) minutes after which the catalyst paste was spread on a pellet plate. The pellet plate was dried in a vacuum oven at 144° C for three hours and then calcined in a muffle furnace for four hours at 540° C.

The dry mixture was prepared by adding the following ingredients together in parts by weight:

$V_2O_5$ — 66.3  
$TiO_2$ — 29.2  
$H_3BO_3$ — 4.5

The final catalyst composition conformed to a mixture, expressed as oxides, of 1 mole $V_2O_5$, 1 mole $TiO_2$, and 0.1 mole $B_2O_3$. The amount of vanadium, expressed as oxide, was 41% by weight. An ammoxidation was carried out under the conditions given in Table II:

TABLE II

Catalyst: Sodium Vanadium Bronze Promoted with Titanium and Boron  
Pressure: 1 Atmosphere  
Contact Time: 1.7 sec.  
Conc. of Hydrocarbon In Feed Stream: 2.8 %

| Temp °C. | Mole Ratio $O_2$:2,6-DMN | Mole Ratio $NH_3$:2,6-DMN | % Conv. | % Selec. | Time (hrs) |
|---|---|---|---|---|---|
| 520 | 4.1 | 33 | 62 | 97 | 1.0 |
| 508 | 4.1 | 31 | 30 | 97 | 5.2 |
| 520 | 4.3 | 30 | 14 | 95 | 11.8 |

As can be seen the high selectivity remained after prolonged on-stream time, thus indicating the valuable contribution made by the process of the invention.

The invention claimed is:

1. In the process of making 2,6-dicyanonaphthalene by reacting 2,6-dimethylnaphthalene, ammonia and oxygen under ammoxidation conditions at atmospheric pressure, the improvement which comprises carrying out said ammoxidation in the presence of an unsupported catalyst selected from the group of an alkali-metal vanadium bronze and an alkali metal-vanadium bronze promoted with titanium, boron or iron and with a molar ratio of ammonia to 2,6-dimethylnaphthalene of at least about 25:1.

2. The process of claim 1 where the catalyst is an alkali metal-vanadium bronze.

3. The process of claim 2 where the catalyst is a sodium-vanadium bronze.

4. The process of claim 1 where the catalyst is a sodium-vanadium bronze promoted with one or more of the oxides of titanium, boron, or iron.

5. The process of claim 2 where the catalyst is Bronze II.

6. The process of claim 4 where the sodium-vanadium bronze is Bronze II.

7. The process of claim 4 where the catalyst is promoted with a mixture of the oxides titanium, boron and iron.

* * * * *